Figure 1:
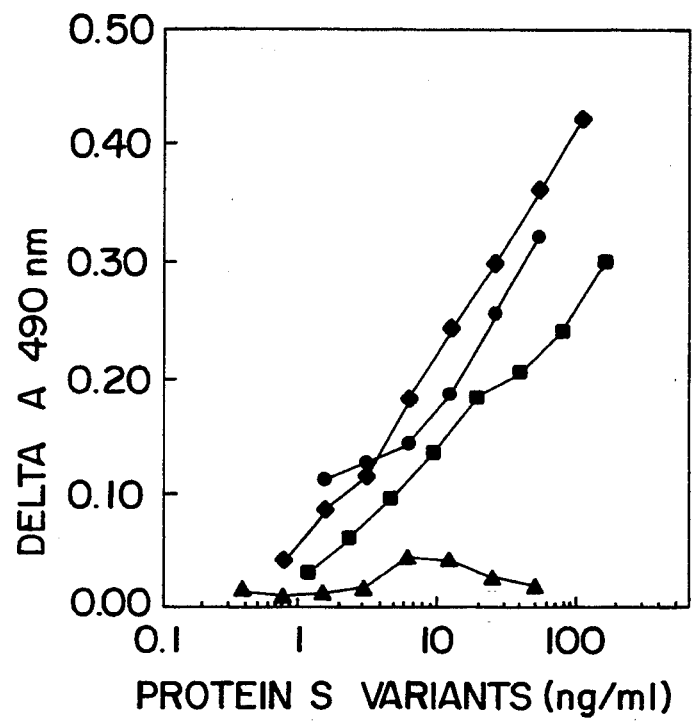

US005405946A

United States Patent [19]

Griffin et al.

[11] Patent Number: 5,405,946
[45] Date of Patent: Apr. 11, 1995

[54] RECOMBINANT PROTEIN S VARIANTS DEFICIENT IN C4BP BINDING ACTIVITY, COMPOSITIONS AND THERAPEUTIC METHODS

[75] Inventors: John H. Griffin, Del Mar, Calif.; Bonno N. Bouma, Baarn; Rogier Bertina, Leiden, both of Netherlands

[73] Assignee: The Scripps Research Institute, La Jolla, Calif.

[21] Appl. No.: 985,691

[22] Filed: Dec. 2, 1992

[51] Int. Cl.[6] ........................ C07K 13/00; C12N 15/12

[52] U.S. Cl. .................................... 530/380; 530/830; 435/69.6; 435/172.3

[58] Field of Search ............................. 435/172.3, 214; 530/380, 381, 829, 830, 395, 350; 514/12, 2

[56] References Cited

PUBLICATIONS

Chang, et al., "The Carboxy Terminal Loop of Human Protein S is involved in the Interaction with Human C4b-Binding Protein", *Blood,* vol. 78, Supp. 1: Abstr. 1099, p. 277a (1991).

Chang, et al., "Characterization of Thrombin-Resistant Variants of Recobinant Human Protein S", *Circulation,* vol. 86, Supp. 1: Abstr. 3241 (1992).

Chang, et al., "Expression and Characterization of Recombinant Human Protein S in Heterologous Cells-Studies of the Interaction of Amino Acid Residues Leu-608 to Glu-612 with Human C4b-Binding Protein", *Thromb. Haemost.,* 67:526-532 (1992).

DiScipio and Davie, "Characterization of Protein S, a γ-Carboxyglutamic Acid Containing Protein from Bovine and Human Plasma", *Biochem,* 18: 899-904 (1979).

Fernandez and Griffin, "Identification of Regions of Protein S Essential For Binding To C4b-Binding Protein", *Thromb. Haemost.,* vol. 65, Supp.: Abstr. 196, p. 711 (1991).

Griffin, et al., "Reevaluation of Total, Free, and Bound Protein S and C4b-Binding Protein Levels in Plasma Anticoagulated with Citrate or Hirudin", *Blood,* 79: 3203-3211 (1992).

Lundwall, et al., "Isolation and Sequence of the cDNA for Human Protein S, a Regulator of Blood Coagulation", *Proc. Natl. Acad. Sci. USA,* 83: 6716-6720 (1986).

Taylor, et al., "C4b-Binding Protein Exacerbates the Host Response to *Escherichia Coli*", *Blood,* 78: 357-363 (1991).

*Primary Examiner*—Robert A. Wax
*Assistant Examiner*—Dian C. Jacobson
*Attorney, Agent, or Firm*—Thomas Fitting

[57] ABSTRACT

The present invention describes a variant protein S protein that is substantially homologous in amino acid residue sequence to wild-type mature human protein S, which has in vitro anticoagulant activity and has a reduced ability to bind C4b binding protein (C4BP), compositions containing the variant protein S, and recombinant DNA vectors for expressing the variant protein. Also disclosed are therapeutic methods of using variant protein S for inhibiting thrombosis, inflammation and the like conditions ameliorated by protein S.

4 Claims, 2 Drawing Sheets

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
    ( A ) LENGTH: 3290 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| CTGGCGCGCC | GCGCAGCACG | GCTCAGACCG | AGGCGCACAG | GCTCGCAGCT | CCGGGCGCCT | 60 |
| AGCTCCGGTC | CCCGCCGCGA | CGCGCCACCG | TCCCTGCCGG | CGCCTCCGCG | GCTCTCGAAA | 120 |
| TGAGGGTCCT | GGGTGGGCGC | TGCGGGGCGT | TGCTGGCGTG | TCTCCTCCTA | GTGCTTCCCG | 180 |
| TCTCAGAGGC | AAACTTTTTG | TCAAAGCAAC | AGGCTTCACA | AGTCCTGGTT | AGGAAGCGTC | 240 |
| GTGCAAATTC | TTTACTTGAA | GAAACCAAAC | AGGGTAATCT | TGAAAGAGAA | TGCATCGAAG | 300 |
| AACTGTGCAA | TAAAGAAGAA | GCCAGGGAGG | TCTTTGAAAA | TGACCCGGAA | ACGGATTATT | 360 |
| TTTATCCAAA | ATACTTAGTT | TGTCTTCGCT | CTTTTCAAAC | TGGGTTATTC | ACTGCTGCAC | 420 |
| GTCAGTCAAC | TAATGCTTAT | CCTGACCTAA | GAAGCTGTGT | CAATGCCATT | CCAGACCAGT | 480 |
| GTAGTCCTCT | GCCATGCAAT | GAAGATGGAT | ATATGAGCTG | CAAAGATGGA | AAAGCTTCTT | 540 |
| TTACTTGCAC | TTGTAAACCA | GGTTGGCAAG | GAGAAAAGTG | TGAATTTGAC | ATAAATGAAT | 600 |
| GCAAAGATCC | CTCAAATATA | AATGGAGGTT | GCAGTCAAAT | TTGTGATAAT | ACACCTGGAA | 660 |
| GTTACCACTG | TTCCTGTAAA | AATGGTTTTG | TTATGCTTTC | AAATAAGAAA | GATTGTAAAG | 720 |
| ATGTGGATGA | ATGCTCTTTG | AAGCCAAGCA | TTTGTGGCAC | AGCTGTGTGC | AAGAACATCC | 780 |
| CAGGAGATTT | TGAATGTGAA | TGCCCCGAAG | GCTACAGATA | TAATCTCAAA | TCAAAGTCTT | 840 |
| GTGAAGATAT | AGATGAATGC | TCTGAGAACA | TGTGTGCTCA | GCTTTGTGTC | AATTACCCTG | 900 |
| GAGGTTACAC | TTGCTATTGT | GATGGGAAGA | AAGGATTCAA | ACTTGCCCAA | GATCAGAAGA | 960 |
| GTTGTGAGGT | TGTTTCAGTG | TGCCTTCCCT | TGAACCTTGA | CACAAAGTAT | GAATTACTTT | 1020 |
| ACTTGGCGGA | GCAGTTTGCA | GGGGTTGTTT | TATATTTAAA | ATTTCGTTTG | CCAGAAATCA | 1080 |
| GCAGATTTTC | AGCAGAATTT | GATTTCCGGA | CATATGATTC | AGAAGGCGTG | ATACTGTACG | 1140 |
| CAGAATCTAT | CGATCACTCA | GCGTGGCTCC | TGATTGCACT | TCGTGGTGGA | AGATTGAAG | 1200 |
| TTCAGCTTAA | GAATGAACAT | ACATCCAAAA | TCACAACTGG | AGGTGATGTT | ATTAATAATG | 1260 |
| GTCTATGGAA | TATGGTGTCT | GTGGAAGAAT | TAGAACATAG | TATTAGCATT | AAAAATAGCTA | 1320 |
| AAGAAGCTGT | GATGGATATA | AATAAACCTG | ACCCCTTTT | TAAGCCGGAA | AATGGATTGC | 1380 |
| TGGAAACCAA | AGTATACTTT | GCAGGATTCC | CTCGGAAAGT | GGAAAGTGAA | CTCATTAAAC | 1440 |
| CGATTAACCC | TCGTCTAGAT | GGATGTATAC | GAAGCTGGAA | TTTGATGAAG | CAAGGAGCTT | 1500 |
| CTGGAATAAA | GGAAATTATT | CAAGAAAAC | AAAATAAGCA | TTGCCTGGTT | ACTGTGGAGA | 1560 |
| AGGGCTCCTA | CTATCCTGGT | TCTGGAATTG | CTCAATTTCA | CATAGATTAT | AATAATGTAT | 1620 |
| CCAGTGCTGA | GGGTTGGCAT | GTAAATGTGA | CCTTGAATAT | TCGTCCATCC | ACGGGCACTG | 1680 |
| GTGTTATGCT | TGCCTTGGTT | TCTGGTAACA | ACACAGTGCC | CTTTGCTGTG | TCCTTGGTGG | 1740 |
| ACTCCACCTC | TGAAAAATCA | CAGGATATTC | TGTTATCTGT | TGAAAATACT | GTAATATATC | 1800 |
| GGATACAGGC | CCTAAGTCTA | TGTTCCGATC | AACAATCTCA | TCTGGAATTT | AGAGTCAACA | 1860 |
| GAAACAATCT | GGAGTTGTCG | ACACCACTTA | AATAGAAAC | CATCTCCCAT | GAAGACCTTC | 1920 |
| AAAGACAACT | TGCCGTCTTG | GACAAAGCAA | TGAAAGCAAA | AGTGGCCACA | TACCTGGGTG | 1980 |

```
GCCTTCCAGA TGTTCCATTC AGTGCCACAC CAGTGAATGC CTTTTATAAT GGCTGCATGG      2040

AAGTGAATAT TAATGGTGTA CAGTTGGATC TGGATGAAGC CATTTCTAAA CATAATGATA      2100

TTAGAGCTCA CTCATGTCCA TCAGTTTGGA AAAAGACAAA GAATTCTTAA GGCATCTTTT      2160

CTCTGCTTAT AATACCTTTT CCTTGTGTGT AATTATACTT ATGTTTCAAT AACAGCTGAA      2220

GGGTTTTATT TACAATGTGC AGTCTTTGAT TATTTGTGG TCCTTTCCTG GGATTTTTAA       2280

AAGGTCCTTT GTCAAGGAAA AAAATTCTGT TGTGATATAA ATCACAGTAA AGAAATTCTT      2340

ACTTCTCTTG CTATCTAAGA ATAGTGAAAA ATAACAATTT TAAATTTGAA TTTTTTTCCT     2400

ACAAATGACA GTTTCAATTT TTGTTTGTAA AACTAAATTT TTAATTTTAT CATCATGAAC     2460

TAGTGTCTAA ATACCTATGT TTTTTTCAGA AAGCAAGGAA GTAAACTCAA ACAAAAGTGC    2520

GTGTAATTAA ATACTATTAA TCATAGGCAG ATACTATTTT GTTTATGTTT TTGTTTTTTT    2580

CCTGATGAAG GCAGAAGAGA TGGTGGTCTA TTAAATATGA ATTGAATGGA GGGTCCTAAT    2640

GCCTTATTTC AAAACAATTC CTCAGGGGGA CCAGCTTGG CTTCATCTTT CTCTTGTGTG     2700

GCTTCACATT TAAACCAGTA TCTTTATTGA ATTAGAAAAC AAGTGGGACA TATTTTCCTG    2760

AGAGCAGCAC AGGAATCTTC TTCTTGGCAG CTGCAGTCTG TCAGGATGAG ATATCAGATT    2820

AGGTTGGATA GGTGGGGAAA TCTGAAGTGG GTACATTTTT TAAATTTTGC TGTGTGGGTC    2880

ACACAAGGTC TACATTACAA AAGACAGAAT TCAGGGATGG AAAGGAGAAT GAACAAATGT    2940

GGGAGTTCAT AGTTTTCCTT GAATCCAACT TTTAATTACC AGAGTAAGTT GCCAAAATGT    3000

GATTGTTGAA GTACAAAAGG AACTATGAAA ACCAGAACAA ATTTTAACAA AAGGACAACC    3060

ACAGAGGGAT ATAGTGAATA TCGTATCATT GTAATCAAAG AAGTAAGGAG GTAAGATTGC    3120

CACGTGCCTG CTGGTACTGT GATGCATTTC AAGTGGCAGT TTATCACGT TTGAATCTAC    3180

CATTCATAGC CAGATGTGTA TCAGATGTTT CACTGACAGT TTTTAACAAT AAATTCTTTT    3240

CACTGTATTT TATATCACTT ATAATAAATC GGTGTATAAT CTAAAAAAAA              3290
```

(2) INFORMATION FOR SEQ ID NO:2:

(i) SEQUENCE CHARACTERISTICS:
        (A) LENGTH: 635 amino acids
        (B) TYPE: amino acid
        (D) TOPOLOGY: linear (ii) MOLECULE TYPE: protein (xi) SEQUENCE DESCRIPTION: SEQ ID NO:2:

```
Ala Asn Ser Leu Leu Glu Glu Thr Lys Gln Gly Asn Leu Glu Arg Glu
 1               5                  10                  15

Cys Ile Glu Glu Leu Cys Asn Lys Glu Ala Arg Glu Val Phe Glu
            20                  25                  30

Asn Asp Pro Glu Thr Asp Tyr Phe Tyr Pro Lys Tyr Leu Val Cys Leu
            35                  40                  45

Arg Ser Phe Gln Thr Gly Leu Phe Thr Ala Ala Arg Gln Ser Thr Asn
 50                  55                  60

Ala Tyr Pro Asp Leu Arg Ser Cys Val Asn Ala Ile Pro Asp Gln Cys
 65                  70                  75              80

Ser Pro Leu Pro Cys Asn Glu Asp Gly Tyr Met Ser Cys Lys Asp Gly
                 85                  90                  95

Lys Ala Ser Phe Thr Cys Thr Cys Lys Pro Gly Trp Gln Gly Glu Lys
            100                 105                 110

Cys Glu Phe Asp Ile Asn Glu Cys Lys Asp Pro Ser Asn Ile Asn Gly
            115                 120                 125

Gly Cys Ser Gln Ile Cys Asp Asn Thr Pro Gly Ser Tyr His Cys Ser
```

```
                    130                          135                          140
Cys   Lys   Asn   Gly   Phe   Val   Met   Leu   Ser   Asn   Lys   Lys   Asp   Cys   Lys   Asp
145                     150                     155                           160

Val   Asp   Glu   Cys   Ser   Leu   Lys   Pro   Ser   Ile   Cys   Gly   Thr   Ala   Val   Cys
                        165                     170                     175

Lys   Asn   Ile   Pro   Gly   Asp   Phe   Glu   Cys   Glu   Cys   Pro   Glu   Gly   Tyr   Arg
                  180                     185                           190

Tyr   Asn   Leu   Lys   Ser   Lys   Ser   Cys   Glu   Asp   Ile   Asp   Glu   Cys   Ser   Glu
            195                           200                     205

Asn   Met   Cys   Ala   Gln   Leu   Cys   Val   Asn   Tyr   Pro   Gly   Gly   Tyr   Thr   Cys
      210                     215                           220

Tyr   Cys   Asp   Gly   Lys   Lys   Gly   Phe   Lys   Leu   Ala   Gln   Asp   Gln   Lys   Ser
225                     230                           235                                 240

Cys   Glu   Val   Val   Ser   Val   Cys   Leu   Pro   Leu   Asn   Leu   Asp   Thr   Lys   Tyr
                        245                     250                           255

Glu   Leu   Leu   Tyr   Leu   Ala   Glu   Gln   Phe   Ala   Gly   Val   Val   Leu   Tyr   Leu
                  260                     265                           270

Lys   Phe   Arg   Leu   Pro   Glu   Ile   Ser   Arg   Phe   Ser   Ala   Glu   Phe   Asp   Phe
            275                     280                     285

Arg   Thr   Tyr   Asp   Ser   Glu   Gly   Val   Ile   Leu   Tyr   Ala   Glu   Ser   Ile   Asp
290                           295                           300

His   Ser   Ala   Trp   Leu   Leu   Ile   Ala   Leu   Arg   Gly   Gly   Lys   Ile   Glu   Val
305                           310                     315                                 320

Gln   Leu   Lys   Asn   Glu   His   Thr   Ser   Lys   Ile   Thr   Thr   Gly   Gly   Asp   Val
                        325                     330                           335

Ile   Asn   Asn   Gly   Leu   Trp   Asn   Met   Val   Ser   Val   Glu   Glu   Leu   Glu   His
                  340                     345                           350

Ser   Ile   Ser   Ile   Lys   Ile   Ala   Lys   Glu   Ala   Val   Met   Asp   Ile   Asn   Lys
            355                           360                     365

Pro   Gly   Pro   Leu   Phe   Lys   Pro   Glu   Asn   Gly   Leu   Leu   Glu   Thr   Lys   Val
      370                     375                           380

Tyr   Phe   Ala   Gly   Phe   Pro   Arg   Lys   Val   Glu   Ser   Glu   Leu   Ile   Lys   Pro
385                     390                           395                                 400

Ile   Asn   Pro   Arg   Leu   Asp   Gly   Cys   Ile   Arg   Ser   Trp   Asn   Leu   Met   Lys
                        405                     410                           415

Gln   Gly   Ala   Ser   Gly   Ile   Lys   Glu   Ile   Ile   Gln   Glu   Lys   Gln   Asn   Lys
                  420                     425                           430

His   Cys   Leu   Val   Thr   Val   Glu   Lys   Gly   Ser   Tyr   Tyr   Pro   Gly   Ser   Gly
            435                           440                     445

Ile   Ala   Gln   Phe   His   Ile   Asp   Tyr   Asn   Asn   Val   Ser   Ser   Ala   Glu   Gly
450                           455                           460

Trp   His   Val   Asn   Val   Thr   Leu   Asn   Ile   Arg   Pro   Ser   Thr   Gly   Thr   Gly
465                           470                     475                                 480

Val   Met   Leu   Ala   Leu   Val   Ser   Gly   Asn   Asn   Thr   Val   Pro   Phe   Ala   Val
                        485                     490                           495

Ser   Leu   Val   Asp   Ser   Thr   Ser   Glu   Lys   Ser   Gln   Asp   Ile   Leu   Leu   Ser
                  500                     505                           510

Val   Glu   Asn   Thr   Val   Ile   Tyr   Arg   Ile   Gln   Ala   Leu   Ser   Leu   Cys   Ser
            515                           520                     525

Asp   Gln   Gln   Ser   His   Leu   Glu   Phe   Arg   Val   Asn   Arg   Asn   Asn   Leu   Glu
      530                     535                           540

Leu   Ser   Thr   Pro   Leu   Lys   Ile   Glu   Thr   Ile   Ser   His   Glu   Asp   Leu   Gln
545                     550                           555                                 560

Arg   Gln   Leu   Ala   Val   Leu   Asp   Lys   Ala   Met   Lys   Ala   Lys   Val   Ala   Thr
                        565                     570                           575
```

```
            Tyr  Leu  Gly  Gly  Leu  Pro  Asp  Val  Pro  Phe  Ser  Ala  Thr  Pro  Val  Asn
                          580                      585                      590

Ala  Phe  Tyr  Asn  Gly  Cys  Met  Glu  Val  Asn  Ile  Asn  Gly  Val  Gln  Leu
                           595                      600                      605

Asp  Leu  Asp  Glu  Ala  Ile  Ser  Lys  His  Asn  Asp  Ile  Arg  Ala  His  Ser
                           610                      615                      620

Cys  Pro  Ser  Val  Trp  Lys  Lys  Thr  Lys  Asn  Ser
                 625                      630                      635
```

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GGAATAAAGA AAATTATTC                                                                               19

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GAAATTATTG AAGAAAAAC                                                                               19

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

ATTCAAGAAG AACAAAATA                                                                               19

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GGAATAAAGG AAGCTGCTCA AGAAAAACAA        30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

GAAAAACAAA ATGAGCACTG CCTGGTTACT        30

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

GATCTCTCGA GGGATCCCTC GAGA        24

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

TGAAAAGAGA GAAGACAAA        19

( 2 ) INFORMATION FOR SEQ ID NO:10:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

GTGGACTGAA GTGCAGCAC        19

( 2 ) INFORMATION FOR SEQ ID NO:11:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

ACACAGCTTA TTAGGTCAG                                                                 19

( 2 ) INFORMATION FOR SEQ ID NO:12:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:12:

Ser Gly Ile Lys Glu Ile Ile Gln Glu Lys Gln Asn Lys His Cys
 1           5                  10                  15

( 2 ) INFORMATION FOR SEQ ID NO:13:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:13:

Ser Gly Ile Lys Lys Ile Ile Gln Glu Lys Gln Asn Lys His Cys
 1           5                  10                  15

( 2 ) INFORMATION FOR SEQ ID NO:14:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:14:

Ser Gly Ile Lys Glu Ile Ile Glu Glu Lys Gln Asn Lys His Cys
 1           5                  10                  15

( 2 ) INFORMATION FOR SEQ ID NO:15:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( v ) FRAGMENT TYPE: internal (x i) SEQUENCE DESCRIPTION: SEQ ID NO:15:

Ser Gly Ile Lys Glu Ile Ile Gln Glu Glu Gln Asn Lys His Cys
1               5                   10                  15

(2) INFORMATION FOR SEQ ID NO:16:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (v) FRAGMENT TYPE: internal (x i) SEQUENCE DESCRIPTION: SEQ ID NO:16:

Ser Gly Ile Lys Glu Ala Ala Gln Glu Lys Gln Asn Lys His Cys
1               5                   10                  15

(2) INFORMATION FOR SEQ ID NO:17:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (v) FRAGMENT TYPE: internal (x i) SEQUENCE DESCRIPTION: SEQ ID NO:17:

Ser Gly Ile Lys Glu Ile Ile Gln Glu Lys Gln Asn Glu His Cys
1               5                   10                  15

RECOMBINANT PROTEIN S VARIANTS DEFICIENT IN C4BP BINDING ACTIVITY, COMPOSITIONS AND THERAPEUTIC METHODS

STATEMENT OF GOVERNMENT SUPPORT

This invention was made with government support under Grant #HL-21544 awarded by The National Institutes of Health. The government has certain rights in the invention.

TECHNICAL FIELD

The present invention relates to various functional variants of recombinant protein S (PS) that do not significantly bind C4b binding protein (C4BP) and uses of the variants as a therapeutic reagent.

BACKGROUND

Protein S (PS) is a vitamin K-dependent protein of 75,000 molecular weight with 635 amino acid residues. DiScipio et al., *Biochem.*, 18:899 (1979); Lundwall et al., *Proc. Natl. Acad. Sci. U.S.A.*, 83:6716–6720 (1986); Hoskins et al., *Proc. Natl. Acad. Sci. U.S.A.*, 84:394–353 (1987). Human plasma contains 346 nM PS of which 62% is complexed with the β chain subunit of complement protein, C4b binding protein (C4BP), and 38% is not complexed to C4BP and considered "free PS". Griffin et al., *Blood*, 79:3203–3211 (1992); Dählback et al., *Proc. Natl. Acad. Sci. U.S.A.*, 78:2512 (1981); Dählback et al., *J. Biol. Chem.*, 265:16082 (1990); and Nelson et al., *Biochemistry*, 30:2384 (1991).

PS exhibits anticoagulant activity in in vitro clotting assays. PS demonstrates anticoagulant cofactor activity for activated protein C (APC), an anticoagulant serine protease enzyme. Walker, *J. Biol. Chem.*, 255:5221–5224 (1980); Harris et al., *J. Biol. Chem.*, 260:2007 (1985); Stern et al., *J. Biol. Chem.*, 261:713 (1986); Walker, *J. Biol. Chem.*, 256:11128 (1981); and Solymoss et al., *J. Biol. Chem.*, 263:14884 (1988). PS has also been shown to be an anticoagulant factor in the absence of APC as it can inhibit prothrombinase activity in assays free of APC, (Mitchell et al., *Thromb. Haemost.*, 60:298–304, 1988), and binds to Factor Va or Factor Xa and functions as an anticoagulant without APC. Heeb et al., *Circulation*, 86:3238a, 1992; and Heeb et al., *Circulation*, 86:1040a, 1992. In plasma, PS reversibly associates with C4BP with high affinity (dissociation constant of about 1–5 nanomolar). Only free PS is active as an APC cofactor and it is widely accepted that the association of PS with C4BP is associated with loss of the anticoagulant activity of PS. Dahlback, *J. Biol. Chem.*, 261:12022 (1986); and Taylor et al., *Blood*, 78:357–363 (1991). Therefore, C4BP is effectively an inhibitor of PS anticoagulant activity. The anticoagulant activity of PS can also be diminished or lost by cleavage at arginine residues within the so-called "thrombin-sensitive loop" comprising residues 46–75. Chang et al., *Circulation*, 86:3241a (1992).

PS is physiologically a very important antithrombotic factor since hereditary or acquired deficiencies of PS are associated with venous and arterial thrombotic disease. Allaart et al., *Thromb. Haemost.*, 64:206 (1990); Sie et al., *Thromb. Haemost.*, 62:1040 (1989); Engesser et al., *Ann. Intern. Med.*, 106:677 (1987); Mannucci et al., *Thromb. Haemost.*, 55:440 (1986); and Schwartz et al., *Blood*, 74:213 (1989). It is widely accepted that because only free PS has anticoagulant activity vitro, the level of free PS in blood in vivo is considered the only relevant physiologic anticoagulantly active species. A deficiency of free PS with a normal level of total PS has been described in some patients with thrombotic disease (Comp et al., *Blood*, 67:504, 1986), and it has been hypothesized that an acquired deficiency of free PS due to temporary elevations of C4BP in disseminated intravascular coagulation or in a wide variety of inflammatory conditions, e.g. systemic lupus erythematosus, may contribute to a hypercoagulable state. Taylor et al., *Blood*, 78:357–363 (1991); Heeb et al., *Blood*, 73:455 (1989); Comp et al., *Blood*, 66:348a (1985); D'Angelo et al., *J. Clin. Invest.*, 81:1445 (1988); Boerger et al., *Blood*, 69:692 (1987); and D'Angelo et al., *Ann. Intern. Med.*, 107:42 (1987). In addition, PS has been suggested to be important in metastasizing carcinoma and leukemias and therefore can be used therapeutically to inhibit cancer cell growth. Kemkes-Matthes, *Clin. Invest.*, 70: 529–534 (1992).

Recently it was shown in an experimental primate animal model that elevations of C4BP exacerbate host response and convert a nonlethal dose of *E. coli* into a lethal dose. Taylor et al., *Blood*, 78:357–363 (1991). It was also shown that treatment of animals receiving excess PS with the C4BP did not suffer the lethal outcome or the hypercoagulable responses, thus showing that free PS which is not bound to C4BP may be a useful therapeutic agent for infection, inflammation and hypercoagulability. Taylor et al., *Blood*, 78:357–363 (1991). Furthermore, Schwarz et al., have described the use of plasma-derived PS in in vivo therapeutic methods for treating thromboses and thromboembolic complications. U.S. Pat. No. 5,143,901.

Forms of PS that have reduced affinity for C4BP would provide useful therapeutic agents since they could be administered without risk of loss of activity associated with binding to C4BP. A variant PS was described by Chang et al., *Blood*, 78:1099a (1991), referred to as the L-variant, in which the carboxy terminal amino acid residues corresponding to residues 583–635 of PS were deleted. The L-variant was shown to retain anticoagulant activity comparable to wild-type PS and to exhibit greatly reduced C4BP binding ability. However, L-variant PS is substantially different from native PS, and may therefore elicit immune responses to those differences upon in vivo administration.

No known recombinant mutants of PS exist which are highly homologous to wild-type PS and which exhibit reduced binding affinity for C4BP species which contain β subunits. This invention provides novel (variant) forms of recombinant PS containing point mutations that have reduced affinity for C4BP, and thereby can exhibit increased serum half life.

BRIEF DESCRIPTION OF THE INVENTION

It has now been discovered that PS can be modified without significant loss of anticoagulant activity by introducing one or more mutations in the region between residues 425 and 432, to reduce significantly or eliminate the ability of PS to bind to C4BP.

The invention describes, in one embodiment, a variant protein S (vPS) having at least 95% amino acid residue sequence identity with wild-type mature human protein S, having in vitro anticoagulant activity and having a capacity to bind C4BP that is less than 95% of the C4BP binding capacity of wild-type mature human protein S. A preferred vPS has one or more amino acid substitutions in the region of 425–432 of mature PS, and a particularly preferred vPS has a substitution selected from the group consisting of K429E, I425A/I426A and K432E.

In a related embodiment, a vPS also contains a mutation in the thrombin sensitive loop region of wild-type mature human protein S defined by residues 45 to 72 of the sequence shown in SEQ ID NO 2, and therefore has thrombin-resistant in vitro anticoagulant activity. Thus, a preferred vPS contains mutations in the 425–432 region, thereby reducing C4BP binding activity, and in the thrombin sensitive region, thereby increasing resistance to cleavage by thrombin. Preferred mutations are amino acid substitutions present in one or more residues at a position in wild-type human protein S selected from the group consisting of position 49, position 60 and position 70. Particularly preferred are the substitutions selected from the group consisting of R49L, R60L and R70I, and more preferably substitutions selected from the group consisting of R49L/R60L, R49L/R70I, R60L/R70I and R49L/R60L/R70I.

Also contemplated are therapeutic compositions comprising a pharmaceutically acceptable excipient admixed with a therapeutically effective amount of a vPS of this invention, and methods for inhibiting coagulation comprising administering to a human patient the pharmaceutical composition.

Further described are DNA segments and recombinant DNA molecules for expressing a vPS of this invention.

BRIEF DESCRIPTION OF THE DRAWINGS

In the drawings forming a portion of this disclosure:

FIG. 1 illustrates the binding of recombinant PS variants having mutations in the first disulfide loop of the sex hormone binding domain of PS to C4BP. The binding assay is described in Example 2B. Anti-C4BP monoclonal antibody 8C11 IgG was coated onto microtiter wells to catch C4BP (1 ug/ml). Recombinant PS (circles), E424K variant (diamonds), Q427E variant (squares) or K429E variant (triangles) were added with increasing amounts in the presence of calcium. Bound PS variants were detected with anti-PS IgG conjugated to peroxidase (0.3 ug/ml). The results are the mean of duplicate values in two different experiments.

FIG. 2 illustrates the functional activity of recombinant PS variant proteins having mutations in the thrombin sensitive domain of PS. The PS-dependent prolongation of the clotting time was measured in an activated partial thromboplastin time system using PS and C4BP depleted plasma, APC and cephalin-kaolin reagent as described in Example 3A. Increasing amounts of recombinant wild-type PS (circles) or the triple variant, R49L/R60L/R70I, (triangles) treated without (open symbols) or with (closed symbols) thrombin were added. Clotting was initiated by the addition of $CaCl_2$ and the clotting time was measured. The results are the means of duplicate values.

FIG. 3 illustrates the binding of variants of PS to C4BP. The binding assay is described in Example 3B. Anti-C4BP monoclonal antibody 8C11 IgG was coated onto microtiter wells to catch C4BP (1 ug/ml). Increasing amounts (0–100 ng/ml) of recombinant wild-type PS (open circles) or variants (R49L, closed diamonds; R60L, closed squares; R70I, closed triangles; R49L/R60L, closed circles; R60L/R70I, open diamonds; R49L/R70I, open squares; R49L/R60L/R70I, open triangles) were added. Binding to C4BP was for 18 hours at room temperature. Bound PS variants were detected with anti-PS IgG conjugated to peroxidase (0.3 ug/ml). The results are the mean of duplicate values in two different experiments.

DETAILED DESCRIPTION OF THE INVENTION

A. Definitions

"Amino acid residue" refers to an amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 C.F.R. 1.822(b)(2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

"Recombinant DNA (rDNA) molecule" refers to a DNA molecule produced by operatively linking two DNA segments. Thus, a recombinant DNA molecule is a hybrid DNA molecule comprising at least two nucleotide sequences not normally found together in nature.

rDNA's not having a common biological origin, i.e., evolutionarily different, are said to be "heterologous".

"Vector" refers to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow convenient expression of a vPS protein of this invention.

B. Variant Protein S

The invention describes a modified (variant or mutant) recombinant protein S, designated vPS, which has the desirable properties of:

(1) anticoagulant activity in in vitro coagulation assays; and (2) reduced ability to bind C4b binding protein (C4BP).

By anticoagulant activity is meant that the vPS has the ability to increase clotting time in standard in vitro coagulation (clotting) assays, preferably by at least 5%, more preferably by at least 10%, and still more preferably by at least from about 20 to 50%. Representative in vitro coagulation assays are described herein.

The ability of an vPS of this invention to bind C4BP is measured in comparison to PS purified from human plasma, or PS produced by recombinant DNA methods, that is, wild-type PS. Preparation of plasma-purified PS has been described by Dahlback et al., *Biochem. J.*, 209:2007–2010 (1983), and by Schwarz et al., U.S. Pat. No. 5,143,901. (The teachings of all references cited are hereby incorporated by reference). Recombinant PS can be produced as described by Chang et al., *Thrombos. Haemost.*, 67:526–532 (1992), or as described herein. A reduced ability of vPS to bind C4BP when compared to wild-type human mature PS binding to C4BP can be any measurable decrease in binding in order to be useful according to this invention, because that reduced binding ability (expressed, for example, as a binding constant) translates into an increased resistance to neutralization by C4BP, an increased plasma level of free proteins, and therefor an effective increase in potency per unit weight of protein.

A preferred reduction in binding ability is at least about 10%, preferably at least about 20%, and preferably at least about a 50 to 99% reduction in binding capacity, when measured in direct binding and expressed as a decrease in binding. Stated differently, vPS has less than about 90%, preferably less than 80%, and more preferably less than about 50 to 1%, of the C4BP binding capacity of wild-type human mature PS when compared in equivalent C4BP binding assays. Binding of vPS to C4BP can be measured by a variety of means. Exemplary C4BP binding assays are described in Example 2A.

A vPS of this invention is preferably substantially homologous to wild-type human mature PS, and preferably retains the full size of the mature PS. Because vPS is to be used, at least in one embodiment, in methods of treatment in vivo, it is important to present to the patient a protein substantially homologous to the native (wild-type) human PS as to limit possible deleterious immune responses to the protein. By substantially homologous is meant at least 95%, preferably at least 98%, and more preferably at least 99%, of the amino acid residues are the same as in wild-type human mature PS. Thus, although the invention describes modified protein S (vPS), the modifications are preferably point mutations (one or more single amino acid residue substitutions) in wild-type PS, thereby minimizing the overall differences of the vPS relative to wild-type PS when viewed by the immune system.

A preferred vPS contains one or more mutations in the amino acid residue sequence within the region of PS between amino acid residues 425 to 432 shown in SEQ ID NO 2 of the mature PS. The complete amino acid residue sequence of mature wild-type human PS is shown in SEQ ID NO 2. Mature PS refers to the protein after cleavage and removal of the leader polypeptide and signal sequence.

Preferred mutations are substitutions of a native (wild-type) amino acid residue by an alternate residue, thereby altering the primary amino acid residue sequence of wild-type PS. Using conventional terminology, a contemplated substitution is indicated by listing the native (wild-type) residue in single letter code followed by the residue position number in the wild-type PS sequence, followed by the substituted amino acid residue. Thus a vPS having a substitution of glutamic acid (E) in place of lysine (K) at residue position number 429 is designated as K429E. A double mutation is designated similarly, but separating each mutation by a slash "/". Thus, a vPS having a substitution of alanine (A) in place of isoleucine (I) at both residue position numbers 425 and 426 is designated as I425A/I426A. Similarly, the substitution of leucine (L) in place of arginine (R) at positions 49 and 60 together with a substitution of isoleucine (I) in place of arginine (R) at position 70 is designated as R49L/R60L/R70I.

Any amino acid residue position within the region of 425 to 432 of PS can be modified for a vPS of this invention, so long as the requisite activity of decreased C4BP binding while preserving anticoagulant activity, is produced. In addition, any amino acid residue can be substituted, so long as the requisite activity is produced. The results herein demonstrate that a variety of different amino acid residues can be substituted, and that a variety of positions can be substituted. Preferred amino acids for substitution include those which provide a hydrophobic cluster, preferably a bulky hydrophobic cluster, such as those forming multiple adjacent hydrophobic residues (e.g., a pair of isoleucines, and the like hydrophobic residues), or a bulky positive charge, such as a lysine or arginine residue.

Preferred positions for substitution are in one or more amino acid positions 425, 426, 429 and 432.

Particularly preferred are the vPS proteins described herein at Examples 1B, 2 and 3, where specific amino acid substitutions were made in the wild-type PS to produce a modified (or mutant) PS (vPS) having the properties described herein.

Thus the invention preferably contemplates a recombinant modified human protein S (vPS) having an amino acid residue sequence consisting of the sequence shown in SEQ ID NO 2 with a substitution selected from the group consisting of K429E, I425A/I426A and K432E.

Insofar as protein S from species other than human are highly related both structurally and in terms of primary sequence, the invention also contemplates mutant protein S having the characteristics of vPS which are derived from other mammals, including cow, rat, rabbit, mouse, pig, primates, and the like. The primary amino acid residue sequence of non-human PS is known for a variety of the recited mammalian species, including human and rhesus monkey.

It has been described by Chang et al., *Circulation*, 86:3241a (1992), that PS can be mutated at certain arginine residues, namely residues 49, 60 and 70 of wild-type PS, to reduce or eliminate the susceptibility of PS to proteolytic cleavages by thrombin which cause loss of anticoagulant activity. Thrombin-sensitive cleavage sites on PS have been identified to reside at residue positions 49, 60 and 70 in the thrombin loop sensitive region, or T-loop region. Thus, substitutions in this regions define a class of mutations referred to as T-loop mutations that form a modified PS. Substitutions of one or more of the residues in the T-loop has been shown to reduce PS susceptibility to thrombin in vitro. Insofar as thrombin cleavage of PS inactivates the anticoagulant activity of PS, inhibition of thrombin sensitivity increases PS activity by increasing its serum half-life. Although the T-loop mutations do not appear to affect the binding of PS to C4BP, mutations in the T-loop do increase resistance to thrombin.

Thus, the invention contemplates in another embodiment, a modified PS in which one or more of PS amino acid residue position numbers 49, 60 or 70 are substituted. By the results described in Example 3, it is seen that multiple substitutions are preferred over single substitutions at conferring thrombin resistance. See, for example, the results described in the Examples herein. Preferred substitutions are those selected from the group consisting of R49L, R60L and R70I. Particularly preferred substitutions are selected from the group consisting of R49L/R60L, R49L/R70I, R60L/R70I and R49L/R60L/R70I. The triple mutant is most preferred.

Thus a preferred vPS of this invention has substitutions in both (1) the region responsible for C4BP binding, i.e., amino acid residue positions 425–432, and (2) the T-loop region as recited herein. Thus a preferred vPS has one or more substitutions in the thrombin sensitive loop, in addition to at least one substitution in the C4BP binding region as defined herein.

A variant protein S (vPS) according to the present invention is used, as discussed further herein, in a variety of therapeutic methods. A vPS can be formulated in therapeutic compositions, and can be administered to inhibit coagulation and other PS-mediated processes.

In addition, a vPS can be used as a reagent to monitor the presence of PS inhibitors other than C4BP based on the ability of vPS to be free of binding to C4BP. Specifically, vPS can be used as a capture or signaling reagent for the presence of PS inhibitors that bind to PS and form a vPS:inhibitor complex. The presence of a complex is detected, indicating the presence of the inhibitor. Thus, vPS is useful as a reagent to screen for the presence of circulating PS inhibitors other than C4BP in the plasma of patients with thrombosis and other coagulation disorders.

C. DNA Segments and Vectors

In living organisms, the amino acid residue sequence of a protein or polypeptide is directly related via the genetic code to the deoxyribonucleic acid (DNA) sequence of the structural gene that codes for the protein. Thus, a structural gene or DNA segment can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

A DNA segment of the present invention is characterized as including a DNA sequence that encodes a mutated human protein S (vPS) according to the present invention. That is, a DNA segment of the present invention is characterized by the presence of a vPS structural gene. Preferably the gene is present as an uninterrupted linear series of codons where each codon codes for an amino acid residue found in the vPS protein, i.e., a gene free of introns.

One preferred embodiment is a DNA segment that codes an amino acid residue sequence that defines a vPS corresponding in sequence to a wild-type PS protein except that the amino acid residue sequence has at least one of the substitutions selected from the group consisting of K429E, I425A/I426A and K432E and the DNA segment is capable of expressing a vPS.

A preferred DNA segment codes for an amino acid residue sequence consisting essentially of the sequence shown in SEQ ID NO 2 except that the sequence shown contains at least one of the substitutions selected from the group consisting of K429E, I425A/I426A and K432E. Representative and preferred DNA segments are described in the Examples.

In a related embodiment, a DNA segment codes for an amino acid residue sequence that defines a vPS corresponding in sequence to a wild-type PS protein described before and that further contains at least one of the substitutions selected from the group consisting of R49L, R60L and R70I, and the DNA segment is capable of expressing a vPS. A particularly preferred DNA segment includes nucleotide sequences that code for a vPS having substitutions selected from the group consisting of R49L/R60L, R49L/R70I, R60L/R70I and R49L/R60L/R70I. In other words, in one embodiment a DNA segment codes for a vPS having substitutions in both the C4BP binding domain and the T-loop, as described herein.

Homologous DNA and RNA sequences that encode the above vPS are also contemplated.

DNA segments (i.e., synthetic oligonucleotides) that encode vPS proteins can easily be synthesized by chemical techniques, for example, the photriester method of Matteucci, et al., (*J. Am. Chem. Soc.*, 103:3185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

Of course, by chemically synthesizing the coding sequence, any desired modifications can be made simply by substituting the appropriate bases for those encoding the native amino acid residue sequence.

Furthermore, a DNA segment consisting essentially of a structural gene encoding vPS can be obtained from recombinant DNA molecules containing a gene that defines wild-type PS, and can be subsequently modified, as by site directed mutagenesis, to introduce the desired substitutions.

Site-specific primer-directed mutagenesis is now standard in the art, and is conducted using a primer synthetic oligonucleotide complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage.

Thus, by site-directed mutagenesis, one can readily construct any of the described DNA segments that code vPS as described herein, by starting, for example, with an expression vector containing the DNA segment shown in SEQ ID NO 1 that codes and expresses wild-type PS, and mutating selected nucleotides, as described herein, to form one or more of the DNA segments that code a vPS of this invention. Exemplary mutagenesis, expression and screening procedures are described in the Examples, and demonstrate the feasibility of producing a vPS of this invention.

In addition, the invention contemplates a recombinant DNA molecule (rDNA) containing a DNA segment of this invention. A rDNA can be produced by operatively linking a vector to a DNA segment of the present invention.

As used herein, the term "vector" refers to a DNA molecule capable of autonomous replication in a cell and to which another DNA segment can be operatively linked so as to bring about replication of the attached segment. A vector capable of directing the expression of a vPS gene is referred to herein as an "expression vector". Thus, a recombinant DNA molecule is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the vPS structural gene included in a DNA segment to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the vPS gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pXT1 available from Stratagene (La Jolla, Calif.), pJ5Eω available from the American Type Culture Collection (ATCC; Rockville, Md.) as accession number ATCC 37722, pTDT1 (ATCC 31255), and the like eucaryotic expression vectors.

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982). Alternatively, the selectable marker can be present on a separate plasmid, and the two vectors are introduced by co-transfection of the host cell, and selected by culturing in the appropriate drug for the selectable marker.

The invention also contemplates a host cell transformed with a recombinant DNA molecule of the present invention. The host cell can be either procaryotic or eucaryotic, although eucaryotic cells are preferred. Eucaryotic cells useful for expression of a vPS protein are not limited, so long as the cell line is compatible with cell culture methods and compatible with the propagation of the expression vector and expression of the vPS gene product. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eucaryotic tissue culture cell lines. Particularly preferred and exemplary is the mouse mammary tumor cell line C127I described by Howley et al., *J. Virol.*, 26:291–298 (1978), and available from the ATCC as ATCC CRL 1616.

Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. U.S.A.*, 69:2110 (1972); and Maniatis et al., *Molecular Cloning, A Laboratory Mammal*, Cold Spring Harbor Laboratory, Cold Spring Harbor, N.Y. (1982).

With regard to transformation of vertebrate cells with vectors containing rDNAs, see, for example, Graham et al., *Virol.*, 52:456 (1973); Wigler et al., *Proc. Natl.*

*Acad. Sci. U.S.A.*, 76:1373-76 (1979), and the teachings herein.

Successfully transformed cells, i.e., cells that contain a rDNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods when the rDNA is capable of directing the expression of vPS, or by the detection of the biological activity of vPS.

For example, cells successfully transformed with an expression vector produce proteins displaying vPS antigenicity or biological activity. Samples of cells suspected of being transformed are harvested and assayed for either vPS biological activity or antigenicity.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying vPS antigenicity or biologically activity.

Nutrient media useful for culturing transformed host cells are well known in the art and can be obtained from several commercial sources. In embodiments wherein the host cell is mammalian, a "serum-free" medium can be used. Preferred is the culturing conditions described herein.

D. Preparation of Variant PS

Variant human protein S (vPS) of this invention can be produced by a variety of means, and such production means are not to be considered as limiting.

Preparation of a vPS typically comprises the steps of: providing a DNA segment that codes a vPS protein of this invention; introduction of the provided DNA segment into an expression vector; introduction of the vector into a compatible host cell; culturing the host cell under conditions sufficient for expression of the vPS protein; and harvesting the expressed vPS protein from the host cell. Exemplary procedures for each of the above-enumerated steps are described in the Examples.

Insofar as the expressed protein is highly related to wild-type PS, the purification of vPS can be conducted by a variety of art-recognized procedures for preparing purified PS from cell culture. See, in particular, the purification procedure described herein.

Thus, in one embodiment, a vPS protein is prepared using a DNA segment as described herein. Alternatively, one can use the screening methods described herein to identify additional substitutions of amino acids in the wild-type PS which produce a vPS having the disclosed desirable properties. As seen by the numerous mutant constructs described herein, a variety of vPS proteins have been designed as produced by the present methods. Additional substitutions (mutations) other than those described specifically herein can be readily designed to form a vPS having the disclosed biological activities. The mutations can be introduced by any of a variety of procedures, such as the in vitro site-directed mutagenesis method described in Example 1B using preselected oligonucleotides.

E. Compositions

A variant human protein S (vPS) of the invention is typically provided in one or more of a variety of compositional forms suitable for the contemplated use. Although vPS retains its biological activity in a variety of buffers and solutions, it is preferred to be formulated in a pharmaceutically acceptable excipient. Particularly preferred are compositions which afford maximum stability and biological activity of the vPS in the composition. Such compositions are generally well known in the art.

In one embodiment, a composition can further contain a therapeutically effective amount of a second active ingredient that is effective as an anticoagulant or thrombolytic agent. A preferred second anticoagulant is protein C (PC) zymogen or activated protein C (APC) when used to coadminister both vPS and PC or APC according to the present methods. Other second anticoagulants can include various heparin preparations and the like. Other anticoagulants can include hirudin, or derivatives or analogs thereof, other anti-thrombin agents (thrombin inhibitors), or tick anti-coagulant protein. A preferred thrombolytic agent includes tissue plasminogen activator, streptokinase, urokinase, and the like.

Insofar as PS is a calcium dependent protein, preferred compositions further contain divalent calcium cation, typically in a physiological amount.

Recombinant vPS may prepared by recombinant technology using methods and expression systems known to the art. See, e.g., Morrissey et al., *Cell* 50:129–135 (1987); and Summers, "A Manual of Methods for Baculovirus Vectors and Insect Cell Culture Procedures," Texas Agricultural Experiment Station, Bulletin 1555 (1987). A preferred method is described herein.

Mutant human protein S may also be purified by immuno-affinity chromatography or other chromatographic methods designed to separate a specific protein from other protein contaminants.

Insofar as the present invention contemplates therapeutic uses of a vPS of this invention, therapeutic compositions useful for practicing the therapeutic methods are preferred. Therapeutic compositions of the present invention contain a physiologically tolerable carrier together with at least one species of vPS as described herein, dissolved or dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

In addition, a therapeutic composition is preferably pyrogen free, i.e., incapable of inducing a pyrogenic response when assayed in conventional assays for pyrogens.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. In addition, a therapeutic amount of vPS can be present in a ointment or on a diffusible patch, such as a bandage, as to afford local delivery of the agent.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water, as described herein. Exemplary of such additional liquid phases are glycerin, vegetable oils such as cottonseed oil, organic esters such as ethyl oleate, and water-oil emulsions.

A therapeutic composition contains an effective amount of vPS of the present invention, typically an amount of at least 0.1 weight percent of active protein per weight of total therapeutic composition. A weight percent is a ratio by weight of vPS protein to total composition. Thus, for example, 0.1 weight percent is 0.1 grams of vPS per 100 grams of total composition.

F. Therapeutic Methods

In view of the demonstrated ability of vPS to act as an anticoagulant, coupled with the reduced or absent C4BP binding activity, a vPS of this invention has the ability to function as a useful anticoagulant with increased plasma levels of free PS due to its relative inability to be inactivated by C4BP. Thus, a vPS of this invention can be used therapeutically in place of wild-type protein S (PS) where PS might be used therapeutically. Typical applications for PS, and particularly a vPS of this invention, include coagulative processes in which PS can function to inhibit coagulation, and particularly those processes where C4BP would be present to inhibit PS.

A representative patient for practicing the present methods is any human at risk for thrombosis, inflammation or other deleterious biological processes in which wild-type PS would provide an ameliorative effect.

Exemplary coagulative processes of particular therapeutic importance for a therapeutic method using vPS include acute thrombosis (both venous and/or arterial), hereditary or acquired protein S deficiency, sepsis, inflammation processes, and cancer. The use of PS in arterial and venous thrombosis is particularly preferred, as indicated by several studies; Green, et al., Neurology, 42: 1029 (1992); Thommen, et al., Schnelz.med Wschr., 119: 493–499 (1989); Wiesel, et al., Thromb. Res., 58: 461–468 (1990).

The method comprises contacting a tissue, organ, body fluid sample such as blood, plasma or serum, or the circulatory system of a patient, in vivo or in vitro, with a composition comprising a pharmaceutically acceptable excipient that contains a therapeutically effective amount of a vPS of this invention. In one embodiment, the contacting in vivo is accomplished by administering a therapeutically effective amount of a physiologically tolerable composition containing a vPS of this invention to a patient.

Thus, the present invention describes in one embodiment a method for inhibiting coagulation in a human comprising administering to the human a composition comprising a therapeutically effective amount of a vPS of this invention.

A therapeutically effective amount of a vPS is a predetermined amount calculated to achieve the desired effect, i.e., to reduce the coagulation time in the body fluid sample of the circulation of the patient, and thereby decrease the likelihood of coagulation. In the case of in vivo therapies, an effective amount can be measured by improvements in one or more symptoms associated with coagulation, inflammation, sepsis or protein S deficiency.

Thus, the dosage ranges for the administration of a vPS of the invention are those large enough to produce the desired effect in which the symptoms of coagulation are ameliorated or the likelihood of coagulation are decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

A therapeutically effective amount of an vPS of this invention is typically an amount such that when administered in a physiologically tolerable composition is sufficient to achieve a plasma or local concentration of from about 1 nanomolar (nM) to 1 micromolar (uM), preferably about 10 to 500 nM, and most preferably about 50 to 200 nM.

The vPS of the invention can be administered parenterally by injection or by gradual infusion over time. The vPS of the invention can be administered intravenously, intraperitoneally, intramuscularly, subcutaneously, intracavity, transdermally, dermally, and can be delivered by peristaltic means. Because coagulation and inflammation are preferred targets for the present methods, intravenous administration to the circulation is a particularly preferred route.

The therapeutic compositions containing a vPS of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Representative therapeutic methods, describing exemplary dosages and routes of administration, using PS that are applicable to the present methods using vPS, are described in U.S. Pat. No. 5,143,901 to Schwarz et al.

In a related embodiment, the invention contemplates the use of vPS in combination with other anticoagulation therapies. In particular, in view of PS as a cofactor to activated protein C (APC), a preferred embodiment utilizes vPS therapeutic compositions in combination with therapeutically effective amounts of protein C (PC) zymogen or APC. PC is known to be converted in vivo to APC, and can therefore be used in place of or in combination with APC in vivo methods. Therefore, in one embodiment the invention contemplates a method of inhibiting coagulation comprising the administration of both a therapeutically effective amount of vPS and a therapeutically effective amount of PC, APC or both, each in a pharmaceutically acceptable excipient. The administration of APC or PC and vPS can be substantially simultaneous (e.g., co-administration), or can be staggered with either vPS or APC (PC) being administered first. Co-administration vPS and APC or PC can be accomplished in a variety of ways. A representative procedure using native PS and APC is described in U.S. Pat. No. 5,143,901 to Schwarz et al, as is the preparation of purified APC suitable for therapeutic use.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Construction of a Recombinant DNA Vector for Expressing Mutant Protein S

A. Cloning and Insertion of Protein S cDNA into a Mammalian Expression Vector

For preparing a protein S (PS) expression vector of this invention, partial cDNAs coding for human protein S were first isolated as described by Ploos van Amstel et al., *FEBS Lett.*, 222:186–190 (1987) from a pUC9 human liver cDNA library. The library, containing $3 \times 10^5$ independent recombinants with an average length insert of 1500 nucleotides, was screened by in situ hybridization with a 27-nucleotide-long oligomer, the sequence of which was derived from a positive clone isolated from a human liver cDNA expression library in lambda gt11 screened with immunopurified polyclonal anti-protein S IgG. Together, the overlapping clones obtained from the screening spanned a partial 5' non-coding region and the complete protein S coding and 3'-untranslated regions. The 3290 nucleotide cDNA sequence is listed as SEQ ID NO 1. The PS nucleotide sequence is also listed in GenBank having the accession number Y00692. The mRNA encodes a preprotein having 676 amino acid residues. After post-translation processing the corresponding translated mature PS consists of 635 amino acid residues as listed in SEQ ID NO 2. The amino acid residue sequence is also listed in GenBank having the accession number A26157.

A full length PS cDNA sequence was obtained by fusion of 2 overlapping partial cDNAs from the two clones, pSUL9 and pSUL11. Clone pSUL9 was first digested with Bgl I and BamH I while clone pSUL11 was digested with Bgl I and Pst I. The desired fragments comprising the entire nucleotide sequence listed in SEQ ID NO 1 were then ligated into the BamH I and Pst I-digested cloning vector pUC18. The resulting plasmid was designated pSUL and the PS sequence was verified by the dideoxy chain termination sequencing method described by Sanger et al., *Proc. Natl. Acad. Sci., U.S.A.*, 76:5463–5467 (1977).

An ACC II/EcoR V cDNA blunt fragment containing the complete PS coding region was isolated from pSUL and cloned into the unique Sma I site of the expression vector pSV328+. The resulting plasmid, designated pSVPS, was subsequently digested with Bgl II and BamH I. The resultant fragment was then ligated into the unique Bgl II site of the plasmid p79-18, a vector similar to plasmid p8-4 described by Sarver et al., in: *Papilloma Viruses: Molecular and Clinical Aspects.* Eds, Howley et al., Alan R. Liss Inc., N.Y., pp 515–527 (1985). The final expression vector containing the complete coding sequence for wild-type human PS was designated pMSVPS. The full length human PS cDNA was flanked 5' by the mouse metallothionein (MMT) promoter and the Moloney murine sarcoma virus (MSV) enhancer elements, and 3' by the Simian Virus SV40 polyadenylation recognition and small t antigen splicing signals.

Other expression vectors for producing wild-type PS, and for the subsequent mutations to produce vPS can also readily be prepared. For example, a DNA segment encoding wild-type PS is made by first preparing synthetic oligonucleotides that define the segment in overlapping complementary oligonucleotide fragments. Thereafter, the fragments are hybridized and ligated to form a complete DNA segment that codes for the precursor form of PS, having a nucleotide sequence shown in SEQ ID NO 1. The termini of the segment are made using oligonucleotides that introduce a preselected restriction endonuclease site for convenient insertion into a preselected expression vector.

In one construction, the oligonucleotide fragments are designed to present BglII termini, and the resulting DNA segment is inserted into the plasmid expression vector pXT1 described by Boutler et al, *Nucleic. Acids*

Res., 17:7194 (1987), available from Stratagene (La Jolla, Calif.), at the BglII site of pXT1, to form pXT1-PS.

In another construction, the oligonucleotide fragments are designed to present BglII termini, and the resulting DNA segment is inserted into the plasmid expression vector pJ5Eω described by Land et al., et al, *Nucleic. Acids Res.*, 18:1068 (1990), available from the American Type Culture Collection (Rockville, Md,) as accession number ATCC 37722, at the BglII site of pJ5Eω, to form pJ5Eω-PS.

In a preferred construction, the bovine papilloma virus (BPV1) genetic element responsible for autonomous, extrachromosomal replication is included in the above vector pJ5Eω-PS. The BPV1 extrachromosomal replication element is obtained from a variety of vectors available from the ATCC, including, but not limited to, pBPV-1(8-2) ATCC 37110, pBPV-BV1 ATCC 37255, and pdBPV-MMTneo(342-12) ATCC 37224. A host eukaryotic cell line used for an expression vector utilizing the BPV extrachromosomal element is the mouse mammary tumor cell line C127I (ATCC CRL 1616) described herein.

B. Site-Directed Mutagenesis of PS

1) Mutagenesis of the First Disulfide Loop of the Sex Hormone Binding Globulin-Like Domain of PS For site-directed mutagenesis of the first disulfide loop in the sex hormone binding globulin-like domain (SHBG) of PS, the pMSVPS expression vector was first digested with Hind III and Bgl II to release a 2808 basepair (bp) fragment containing the PS cDNA sequence. The fragment was then subcloned into M13mp19 for mutagenizing according to the uracil substitution method described by Kunkel, *Proc. Natl. Acad. Sci., U.S.A.*, 82:488–492 (1985) also described in Ausebel et al., *Current Protocols in Molecular Biology*, Unit 8, Wiley and Sons, New York, (1990). The M13mp19 clone carrying the PS insert was infected into CJ236/p3 (dut⁻ung⁻) (Bio-Rad Corp., Richmond, Va.) and uracil-containing single stranded phage DNA was isolated and used as a template for mutagenesis. Phosphorylated mutagenic oligonucleotides (10 nanograms (ng)) were separately annealed to the isolated single-stranded template (100 ng) in 20 mM Tris-HCl at pH 7.4, 2 mM MgCl$_2$, 50 mM NaCl at 70 degrees Celsius (70C.) and cooled to room temperature. The second strand was synthesized using T4 DNA polymerase and T4 DNA ligase (Boehringer Mannheim, Indianapolis, Ind.) in 10 mM Tris-HCl at pH 7.5, 5 mM MgCl$_2$, 2 mM dithiothreitol, 5 mM deoxynucleotide triphosphates and 10 mM ATP for 5 minutes at 4C., 5 minutes at room temperature, and 90 minutes at 37C. One-fifth of the reaction was then transformed into competent *E. coli* XL-1 blue (dut+ung+) (Stratagene, La Jolla, Calif.) and transformants were screened for the presence of mutant sequences by sequencing by the dideoxy chain termination method of Sanger et al., supra. Sequencing of mutant constructs was accomplished using single-stranded DNA rescued with the helper phage R408. The Sequenase Version 2.0 system (U.S. Biochemical, Cleveland, Ohio) was used to perform dideoxynucleotide sequencing.

The following oligonucleotides listed in the 5' to 3' direction were used in the above mutagenesis procedure to obtain the corresponding identified mutated PS variant. The nucleotide for introducing the desired amino acid substitutions at the locations indicated in the PS variant are underlined. The letters before and after the identified amino acid residue position of the mature PS protein respectively indicate the normal amino acid residue and the introduced mutation. For the E424K variant—5'-GGAATAAAGAAAATTATTC-3' (SEQ ID NO 3); for the Q427E variant—5'-GAAATTATTGAAGAAAAAC-3' (SEQ ID NO 4); for the K429E variant—5'-ATTCAAGAAGAACAAAATA-3' (SEQ ID NO 5); for the I425A/I426A variant—5'-GGAATAAAGGAAGCTGCTCAAGAAAAACAA-3' (SEQ ID NO 6); and for the K432E variant, a representative oligonucleotide that would amplify the desired mutation is—5'-GAAAAACAAAATGAGCACTGCCTGGTTACT-3' (SEQ ID NO 7) The amino acid residue positions are shown in SEQ ID NO 2 listing the amino acid residue sequence of the mature PS.

Following verification of the mutated sequence variants, double-stranded phage DNA was then isolated from the bacterial cells and a part of the protein S insert containing the mutated sequences was isolated after Sal I and Xba I digestion. The PS insert was then operatively ligated into the original mammalian expression vector, pMSVPS, that was previously digested with the same restriction enzymes. Into the pMSVPS expression vectors, each containing a mutated PS nucleotide sequence, was ligated a bovine papilloma virus (BPV) genome to prepare a shuttle vector under the transcriptional control of the MSV enhancer and MMT promoter.

Cloning of the BPV-1 genome into both the native or wild-type PS-containing vector and the pMSVPS PS-variant-containing vectors was performed as described by Chang et al., *Thromb. Haemost.*, 67:526–532 (1992). In order to facilitate the growth and production of full length viral BPV-1 genome in bacteria, pTZX was first constructed from pTZ18R by digesting pTZ18R (Bio-Rad Corp.) with BamH I and inserting the following partially self-complementary oligonucleotide 5'-GATCTCTCGAGGGATCCCTCGAGA-3' (SEQ ID NO 8). In pTZX, a BamH I site was then flanked by two Xho I sites, while the reading frame was still intact. The full length vital BPV-1 genome was the digested at the unique BamH I site and inserted into the BamH I digested pTZX to yield the plasmid pTZX-BPV. The resulting full length bacterial BPV-1 genome was then digested from pTZX-BPV using either BamH I or Xho I. The pMSVPS expression vectors containing either wild-type or variant PS sequences were then separately digested with BamH I and ligated with BamH I-digested bacterial BPV-1 genome. The resultant vectors separately contained full length human PS, either wild-type or mutated variants as described herein, under the transcriptional control of the MMT promoter and the MSV enhancer. In addition, the transcription unit contained the small t intron and early polyadenylation signal from SV 40 and the entire BPV genome.

2) Mutagenesis of the Thrombin-Sensitive Domain of PS

To construct PS variants in the thrombin-sensitive domain, site-directed mutagenesis was performed as described above with the following exceptions: 1) A 430 bp BamH I/Hind III fragment from the expression vector pMSVPS carrying a part of the protein S cDNA sequence was subcloned into M13mp19; 2) For the R49L variant, the oligonucleotide 5'-TGAAAAGAGAGAAGACAAA-3' (SEQ ID NO 9) was used; 3) For the R60L variant, the oligonucleotide 5'-GTGGACTGAAGTGCAGCAC-3' (SEQ ID NO 10) was used; 4) For the R70I variant, the oligonucleotide 5'-ACACAGCTTATTAGGTCAG-3' (SEQ ID NO 11) was used; and 5) For the double and triple variants, combination of two or three oligonucleotides were used. The amino acid residue positions 49, 60 and 70 are shown in SEQ ID NO 2 listing the amino acid residue sequence of mature PS.

C. Production of Wild-Type and PS-Variant-Producing Stable Transformants

In order to obtain stable cell lines for producing the recombinant mutated PS variant proteins of this invention, the expression vectors containing mutagenized PS sequences prepared in Example 1B were separately transfected into C127I cells (ATCC Accession Number CRL 1616). The same procedure was performed for the expression of recombinant wild-type full length PS. The cells were first cultured in Iscove's Modified Dulbecco's Medium, supplemented with penicillin G (100 Units/milliliter (U/ml), streptomycin sulphate (100 micrograms/ml (ug/ml), glutamine (2 millimolar (mM)), 50 micromolar (uM) beta-mercaptoethanol, trasylol (10 U/ml) (Bayer, Leverkusen FRG) and 10% heat-inactivated fetal bovine serum. The remaining cell culture reagents were purchased from Gibco (Paisly Park, UK). Cell cultures were maintained at 37C. in a humidified incubator containing 5% $CO_2$. One day prior to transfection, cells were trypsinized and seeded with a density of $5 \times 10^5$ cells/10 centimeter dish containing 10 ml complete medium.

For transfections, 20 ug of variant plasmids and wild-type plasmids were separately transfected into the cultured cells using a conventional calcium phosphate coprecipitation technique as described by Graham et al., *Virol.*, 52:456–467 (1983). Briefly, the DNA-calcium phosphate precipitate was formed during a 20 minute incubation at room temperature and added to the cells. Transfections were carried out overnight in the incubator. Following the transfections, the cells were washed twice with 10 mM sodium phosphate at pH 7.4 containing 2.7 mM KCl and 150 mM NaCl in PBS. The cells were then maintained in complete medium after which time they were washed, trypsinized and seeded at a 1:5 ratio and maintained in medium containing only 5% fetal bovine serum. Cells were fed every 3–4 days in medium containing 5% fetal bovine serum until foci were visible, usually 12–14 days after subculturing. Foci were then isolated, grown individually and subcloned using limiting dilution (1 cell/well).

D. Expression and Verification of Wild-type and PS Variants

Expression of gamma-carboxylated wild-type PS and PS variant proteins was initiated in the foci prepared in Example 1C by growing the cells in DMEM containing 5 ug/ml Vitamin $K_1$ (Konakion, Roche) without serum. The level of expression varied between 0.1 to 1 ug/ml.

The cultures were then assayed for either wild-type or mutant PS antigen using an ELISA as described by Deutz-Terlouw et al., *Clin. Chim. Acta.*, 186:321–334 (1989). Briefly, the expressed wild-type PS and PS variant proteins were measured by a double polyclonal ELISA using rabbit anti-PS IgG as catching antibody and rabbit anti-PS IgG conjugated to peroxidase as tagging antibody. Titertek assay plates (Titertek) were coated with 110 ul/well of polyclonal anti-PS IgG solution, containing 1.5 mg/ml immunopurified anti-PS IgG and 18.5 mg/liter nonspecific rabbit IgG in 0.1M $NaHCO_3$ at pH 9.0 containing 0.5M NaCl. The plates were maintained for 12 hours at 4C. to allow the antibody to adhere to the well walls.

Before use, the assay plates were washed 5 times with wash buffer (67 mM $Na_2HPO_4$, 14 mM $KH_2PO_4$, 0.1% Tween-20 at pH 7.5), maintained for 30 minutes at room temperature with 150 ul/well of a solution containing 20 grams/liter (g/l) bovine serum albumin (BSA) in wash buffer, and washed 5 times again with wash buffer. Subsequently, 100 ul of PS variant culture supernatant were added to the wells and maintained for 18 hours at room temperature. The long maintenance period was necessary to favor complete dissociation of complexed PS and allow the PS to bind to the anti-PS coating the wells. Assay plates were then washed 5 times with wash buffer after which 100 ul/well of horse radish peroxidase-labeled anti-PS IgG was added to each well. The enzyme-labeled detecting antibody was maintained for 45 minutes at room temperature in the assay plates, after which the plates were washed 5 times with wash buffer. The bound detecting antibody was detected with 100 ul/well of 2.2 mM ortho-phenylenediamine dihydrochloride (OPD), 0.12 ml/liter hydrogen peroxide, 22.2 mM citric acid and 51.4 mM $NaH_2PO_4$—$H_2O$ at pH 5.0. After stopping the reaction at 30 minutes, the absorbance was measured at 492 nm using a multichannel analyzer (EL 312 Microplate reader, Bio-Tek Instruments, Inc., Winooski, Vt).

E. Purification of Protein S Variants and Immunoblotting Analysis

For purification of selected recombinant PS variants and PS wild-type recombinant protein for use in subsequent assays, the PS-expressing clones prepared and screened in Example 1D were expanded in medium containing 10% fetal bovine serum and grown to confluency. Thereafter, the culture medium was replaced with medium containing 5 ug/ml vitamin K1 lacking serum to initiate the expression of PS that was maintained over a 48 to 72 hour period. Culture medium was then harvested and stored at −20C. until purification.

Protein S variants were purified on an anion-exchange column (Fast Flow Q resin, Pharmacia) as described by Chang et al., supra. The collected supernatants (500 ml each) containing PS variants were supplemented with 25 ml 1M sodium citrate (final concentration of 50 mM). Fifty ml 1M $BaCl_2$ was then added slowly for a final concentration of 100 mM while stirring on ice. The barium citrate precipitate was collected after 30 minutes by centrifugation at 5000 rpm for 10 minutes, dissolved in 50 ml 100 mM Tris-HCl at pH 7.5 containing 100 mM EDTA, and dialyzed extensively against 50 mM sodium citrate, reprecipitated by the addition of 5 ml 1M $BaCl_2$, dissolved in 5 ml 100 mM Tris-HCl at pH 7.5 containing 100 mM EDTA and finally dialyzed extensively against 50 mM Tris-HCl at pH 7.5 containing 150 mM NaCl. The dialysate was further purified on an anion exchange Fast Flow Q resin column (2 ml) by adsorbing the PS to the column in starting buffer containing 2 mM EDTA, washed with the same buffer without EDTA and eluted with the same buffer containing 5 mM $CaCl_2$. The fractions containing recombinant PS variants were separately pooled, dialyzed against the starting buffer and stored at −20C.

The purity and integrity of the recombinant PS variants was established by SDS-PAGE on 12.5% gradient gels according to Laemmli, *Nature*, 227:680–685 (1970) using the Phast system (Pharmacia Biotechnology, Sweden). After electrophoresis, the proteins were stained with silver nitrate or transferred onto Immobilon membranes for subsequent detection by Western blot analysis using rabbit anti-PS IgG conjugated to peroxidase (3 ug/ml).

For the thrombin-sensitive PS variant proteins, on reduced SDS gels, purified recombinant PS and the single and double variants all migrated as a doublet. In the case of the triple variant only one band was observed at the height of the upper band of the doublet. The upper band of the doublet for recombinant PS and the single and double variants all could be converted into the lower band by thrombin treatment. The band of the triple variant however, was not converted into a lower band, indicating that this triple variant was resistant to thrombin. The observation that the single chain form (upper band) of all three double variants could be converted into two-chain forms (lower band) indicates that all three potential cleavage sites can be hydrolyzed by thrombin.

2. Characterization of PS Variants in the First Disulfide Loop of the Sex Hormone Binding Globulin-Like Domain A. Binding of Recombinant PS Variants to C4BP Human PS forms a reversible complex with human C4b-binding protein (C4BP), the result of which down-regulates the APC cofactor activity of PS, because only free protein S is active as a cofactor to APC. Several reports have shown that the second disulfide loop of the C-terminal end of the SHBG-like domain (amino acid residues 583–636 of SEQ ID NO 2) of protein S is involved in its binding to C4BP. Later studies raised the possibility that this region was an essential element in maintaining the correct protein structure for a binding site located elsewhere in the PS molecule. The presence of an alternative binding site in the first disulfide loop of the SHBG-like domain (amino acid residues 420–434 of SEQ ID NO 2) was reported by Fernandez et al., *Thromb. Haemost.*, 65:711 (1991). The recombinant PS variants of this invention were used to study the interaction of PS and C4BP in the first disulfide loop region. The results with the recombinant PS variants were compared with results where the corresponding synthetic PS peptides were used. The latter is presented in Example 2B.

The complex formation between the recombinant PS variant proteins and C4BP was measured with a sensitive ELISA using C4BP and a peroxidase conjugated anti-PS antibody as described by Chang et al., *Thromb. Haemost.*, 67:526–532 (1992). Briefly, IgG at a concentration of 10 ug/ml from monoclonal antibody 8C11, which is directed against the alpha chain of C4BP (Hessing et al., *J. Immunol.*, 144:204–208 (1990), was coated in 50 mM NaHCO$_3$ at pH 9.6 overnight at 4C. onto polyvinyl microtiter plates (Costar, Cambridge, Mass.). After washing to remove the unbound IgGs, the wells were blocked with 1% (w/v) BSA in 50 mM Tris-HCl at pH 7.5 containing 150 mM NaCl and 5 mM CaCl$_2$ for 1 hour at room temperature. C4BP, prepared as described by Hessing et al., supra, was allowed to bind for 2 hours with a final concentration of 1 ug/ml. Increasing amounts of recombinant PS proteins (E424K, Q427E, K429E, I425A/I425A and K432E) and wild-type recombinant PS prepared in Example 1 were then added in concentrations ranging from 0–150 ng/ml and maintained for 18 hours at room temperature. Bound proteins were allowed to bind to rabbit anti-human PS IgG conjugated to peroxidase (Dako-patts, Glostrup, Denmark) at a concentration of 0.3 ug/ml for 2 hours at room temperature. After washing the wells to remove the unbound proteins, 100 ul of 0.1M sodium phosphate/0.2M sodium citrate at pH 5.0 containing 0.04% 1,2-phenylenediamine dihydrochloride and 0.015% hydrogen peroxide was added. The hydrolysis of phenylenediamine was stopped by adding 50 ul 2N sulfuric acid. The absorbance was measured at 490 nm using a V$_{max}$ plate reader (Molecular Devices Corp., Menlo Park, Calif.). The data represented the mean of duplicate determinations.

The results of the binding assays shown in FIG. 1 revealed that the E424K and Q427E PS variants bound to C4BP with the same apparent affinity as the wild type recombinant molecule, suggesting that replacement of Glu-424 by Lys or Gln-427 by Glu has no effect on the binding and therefore are not required for binding to C4BP. The K429E, I425A/I426A and K432E PS variants failed to bind to C4BP at concentrations up to 50 ng/ml. These results suggest that Lys-429, Ile-425, ILe-426 and Lys-432 are necessary amino acid residues for binding to C4BP. These same results were obtained with synthetic PS peptides as described below.

B. Binding of C4BP to Synthetic PS Peptides

Synthetic peptides listed in Table 1, each with 15 amino acid residues, were produced by the simultaneous multiple peptide synthesis method described by Houghton, *Proc. Natl. Acad. Sci., U.S.A.*, 82:5131–5135 (1985). All peptides were synthesized in the carboxy terminal amide form. After synthesis, the peptides were analyzed by reverse-phase high performance liquid chromatography (HPLC) on a Vydac C-18 column (Alltech Associates, Inc. Ill.) with a 0.6% acetonitrile linear gradient in 0.1% trifluoroacetic acid. Peptides were purified to homogeneity by preparative HPLC using the best conditions suggested by the analytical chromatography. Amino acid compositions and concentrations of isolated peptides were determined by subjection to 24 hour hydrolysis in 6N HCl in evacuated tubes at 110C. Subsequent analysis of peptides using the FIB positive ion mass spectra obtained on a VG-ZAB-VSE double focusing mass spectrometer equipped with a cesium ion gun yielded a single peak and an exact expected molecular weight. Solutions of each peptide were prepared as described by Mesters et al., *J. Biol. Chem.*, 266:24514–24519 (1991).

TABLE 1

| Peptide Designation | SEQ ID NO | Amino Acid Sequence |
| --- | --- | --- |
| PSP-420 | 12 | SGIKEIIQEKQNKHC |
| E424K | 13 | SGIKKIIQEKQNKHC |
| Q427E | 14 | SGIKEIIEEKQNKHC |
| K429E | 15 | SGIKEIIQEEQNKHC |
| I425A/I426A | 16 | SGIKEAAQEKQNKHC |
| K432E | 17 | SGIKEIIQEKQNEHC |

For the assay to measure the binding of C4BP to the PS synthetic peptides listed in Table 1, 50 ul of the different synthetic peptides (20 uM) or native PS (10 ug/ml) (prepared as described by Keodam et al., *J. Clin. Invest.*, 74:2082–2088 (1984) were diluted in 0.02M sodium carbonate buffer at pH 9.0. They were then separately added to wells of a microtiter plate for 1 hour at 37C. to allow the peptides to adhere to the well walls. The wells were then blocked with 200 ul of 10% BSA in 0.05M Tris-HCl at pH 7.4 containing 0.1M NaCl (TBS). Wells were then washed 3 times with 0.2% BSA in TBS, 5 mM CaCl$_2$ and 0.02% Tween 20 (washing buffer). Serial dilutions containing 50 ul biotinylated C4BP (bC4BP) (0-5 ug/ml in washing buffer) were added to each well and maintained for 2 hours at room temperature to allow the C4BP to bind to the solid-phase peptides.

After the wells were washed 3 times with washing buffer, 50 ul/well of streptavidin conjugated to alkaline phosphatase (SAAP, Pierce Biochemicals, Rockford, Ill.) (1 ug/ml diluted in washing buffer) was added and maintained for 30 minutes at room temperature to allow for the binding of the detecting reagent to the biotin-labeled C4BP. Wells were then washed 6 times and 100 ul of p-nitrophenylphosphate (p-NPP) (Pierce) (5 mg/ml in 0.1M diethylamine buffer at pH 9.0) was then added to each well. The change in absorbance at 405 nm was detected using EL 312 Microplate (Bio-Tek Instruments, Inc.). Results of the assays were given as the change in absorbance (delta A) at 405 nm/minute. Each sample was assayed in duplicate and the results were averaged.

In this assay, maximal binding of C4BP to peptide E424K plateaued with approximately 2.5 ug/ml bC4BP at an absorbance of 140 ($\times 10^{-3}$) in a saturating curve similar to that seen with native PS used at 10 ug/ml. PSP-420 bound weaker than the E424K peptide which saturated at 2.5 ug/ml bC4BP at an absorbance of 90 ($\times 10^{-3}$) but stronger than the Q427E peptide which also saturated at 2.5 ug/ml bC4BP but with an absorbance of 60 ($\times 10^{-3}$). The K429E, I425A/I426A and K432E peptides failed to bind to C4BP at any concentration of bC4BP tested. Thus, these results support those seen with the recombinant PS variants described in Example 2A.

C. Competition of Synthetic PS Peptides and Native PS for C4BP

The ability of the synthetic PS peptides to compete with native PS for binding to C4BP was studied in solid and fluid phase competition assays. In the first solid phase inhibition assay, a mixture of bC4BP and synthetic peptides prepared in Example 2B was added to PS that was previously immobilized onto microtiter wells. In the second assay referred to as a fluid phase inhibition assay, a mixture of bC4BP, PS and synthetic peptides was added to an immobilized anti-PS monoclonal antibody, designated S7, that did not interfere with the binding of PS to C4BP.

For the solid phase inhibition assay, bC4BP at 0.5 ug/ml had been maintained with serial dilutions of synthetic peptides ranging in concentration from 0-500 uM for 1 hour at room temperature. From this mixture, 50 ul was added to a microtiter plate coated with 50 ul of native PS (10 ug/ml) in 0.02M sodium carbonate buffer at pH 9.0 for 1 hour at 37C. and blocked with 200 ul of 10% BSA in 0.05M Tris-HCl at pH 7.4 containing 0.1M NaCl (TBS).

For the fluid phase inhibition assay, bC4BP (0.5 ug/ml) and native PS (1 ug/ml) had been maintained with serial dilutions of synthetic peptides ranging in concentration from 0-500 uM for 1 hour at room temperature. From this mixture, 50 ul was added to a microtiter plate that was previously coated with IgG of an anti-PS monoclonal antibody (S7) at 10 ug/ml in 0.02M sodium carbonate buffer at pH 9.0 for 1 hour at 37C. and blocked with 10% BSA in TBS buffer.

For both assays, the wells were washed 3 times with 0.2% BSA in TBS, 5 mM CaCl$_2$ and 0.02% Tween 20 (washing buffer), and 50 ul SAAP at 1 ug/ml concentration diluted in washing buffer was then added and maintained for 30 minutes at room temperature to allow for the binding of the detecting reagent to biotinylated C4BP. Wells were washed 6 times with washing buffer and 100 ul p-NPP at 5 mg/ml concentration in 0.1M diethylamine buffer at pH 9.0 was added to each well. The change in absorbance at 405 nm was detected kinetically using an EL 312 Microplate reader. Results of the assay were given as the change in absorbance at 405 nm/minute.

In both the fluid phase and solid phase inhibition assays the PSP-420 and E424K peptides, at a concentration of 200 uM, maximally inhibited the binding of C4BP to PS (approximately 15% C4BP bound in the presence of 100-200 uM peptide). The Q427E peptide was more effective at inhibiting the binding of C4BP to PS in the solid phase (approximately 60% C4BP binding with 400-600 uM peptide) as compared to the fluid phase assay where no inhibition of binding was detected. The normal Gln-427 amino acid residue of PS thus is weakly involved in the binding of PS to C4BP in the solid phase but more critically involved in the fluid phase assay. The K429E variant peptide did not compete for the binding of PS with C4BP in either assay indicating that the normal Lys-429 amino acid residue is involved in the binding of PS to C4BP.

D. Cofactor Activity of Recombinant PS Variants with APC in a Clotting Assay

An activated partial thromboplastin time clotting assay, using PS- and C4BP-depleted plasma, cephalin-kaolin reagent (Boehringer Mannhein, Indianapolis, Ind.), activated protein C (APC) and increasing amounts of recombinant PS variants was performed as described by Chang et al., *Thromb. Haemost.*, 67:526-532 (1992). Briefly, to 50 ul PS and C4BP-depleted plasma (prepared as described by Koedam et al., *J. Clin. Invest.*, 82:1236-1243 (1988)) was added 50 ul cephalin-kaolin reagent, 25 ul APC (Koedam et al., ibid) at 5 ug/ml and 15 to 45 ul recombinant PS variants (0-4 ug/ml) diluted in Michaelis buffer (28.5 mM sodium acetate, 28.5 mM sodium barbital and 116 mM NaCl, pH 7.35) and maintained for 3 minutes at 37C. Clotting was initiated by addition of 50 ul of 25 mM CaCl$_2$ and the clotting time was measured in an Amelung-Coagulometer KC10.

The results plotted in Table 2 were compared with clotting times in the presence of recombinant PS wild type at 2.4 ug/ml.

TABLE 2

| PS Variant Designation | Clotting Time (sec) | Final Conc. (ug/ml) |
|---|---|---|
| E424K | 97 | 0.6 |
| Q427E | 94 | 0.6 |
| K429E | 88 | 1.8 |
| rPS wild-type* | 116 | 2.4 |
| Basal clotting | 80 | |

*Recombinant wild-type PS

The clotting time data indicates that all recombinant PS variants, in comparison with the basal clotting time of 80 seconds, significantly inhibited clotting and therefore exhibited functional anticoagulant activity. In addition, when the K429E PS variant was assayed in increasing amounts, the anticoagulant activity increased linearly with increasing volumes of variant PS where the maximal inhibition of clotting occurred at approximately 95 seconds. Thus, the recombinant PS variants not only fail to bind to C4BP but also exhibit anticoagulant properties. These combined properties allow PS variant proteins as well as PS peptides of this invention to be free to act as cofactors to APC in the inactivation of coagulation factors Va and VIIIa without coordinate depletion by complexing with C4BP as occurs with native PS.

E. Affinity of Anti-PS Monoclonal Antibody LJ-56 for Synthetic PS Peptides and Recombinant PS Variants An anti-PS monoclonal antibody, designated LJ-56, was raised against the PSP-420 peptide and was shown to only recognize free PS and inhibit the binding of PS to C4BP. To determine the affinity of this antibody for the synthetic PS peptides and recombinant PS variant proteins of this invention, binding assays were performed as described herein.

For measuring the affinity of LJ-56 for the synthetic PS peptides, microtiter wells were separately coated with 50 ul of the peptides prepared in Example 2B (20 uM, 50 ug/ml) in 0.02M sodium carbonate buffer at pH 9.0 for 2 hours at room temperature. Wells were then blocked with 200 ul of 10% BSA in TBS and subsequently washed with 0.2% BSA and 0.02% Tween-20 in TBS. LJ-56 (292 ug/ml) was then added to each well and maintained for 1 hour at room temperature at dilutions ranging from 1/100 to 1/12,8000 to allow the antibody to immunoreact with the peptides. Wells were then washed and maintained with 50 ul biotinylated rabbit anti-mouse IgG (1 ug/ml) for 1 hour at room temperature to allow for the detection of the immunoreactant products. Wells were then washed and 50 ul SAAP (1 ug/ml) was added to each well followed by maintenance for 30 minutes at room temperature to allow the avidin detecting reagent to bind to the biotinylated secondary antibody. Wells were then washed and 100 ul of p-NPP (5 mg/ml) was added. The change of absorbance was measured as previously described.

LJ-56 recognized the PSP-420 peptide, the E424K and Q427E peptides with equal affinity but failed to bind to K429E. These results suggest that Lys-429 is important for the recognition by LJ-56. Reactivity of LJ-56 to the recombinant PS variant proteins gave essentially the same results when a sandwich detecting assay was performed. In the sandwich assay, a fixed amount of recombinant PS variants produced in Example 1B1) (50 ng for E424K and 100 ng for wild type, Q427E and K429E) were added to wells previously coated with rabbit anti-PS IgG at 10 ug/ml in coating buffer and treated to block nonspecific binding sites as described above. Following a maintenance period for 18 hours at room temperature, the wells were washed with TBS and 100 ul of serial dilutions of anti-PS monoclonal antibody LJ-56 (0–10 ug/ml) was added and maintained for 2 hours at room temperature. Detection of the immunoreactant products was accomplished with rabbit anti-mouse IgG conjugated to peroxidase (1:1000). The hydrolysis of nitrophenylphosphate was measure at 490 nm using a $V_{max}$ plate reader as described in Example 2A.

The results of the sandwich assay with the recombinant PS variant proteins showed that LJ-56 recognized the E424K and Q427E variants similar to that seen with wild type recombinant PS protein, whereas the K429E variant was not recognized. The substitution of Lys-429 by Glu probably induces a conformational change in both the variant proteins as well as in the synthetic peptide resulting in a loss of recognition by LJ-56. The results indicate that Lys-429 of PS is essential for the binding of C4BP and for the recognition of LJ-56.

Thus, the recombinant PS variant proteins and PS synthetic peptides of this invention allow for the investigation of the contribution of individual amino acid residues in the overall function of PS. The PS peptides functioned similarly to the recombinant PS variant proteins suggesting that the mutant peptides are in the same conformation as their corresponding sequences in the recombinant protein variants. Both compositions are effective at mediating the preferred anticoagulant properties without depletion by complexation with C4BP. The properties of the compositions of this invention provide for the requisite therapeutic benefits of ameliorating thrombosis by enhancing the anticoagulant properties of APC without depletion by C4BP binding.

3. Characterization of PS Variants in the Thrombin-Sensitive Domain

From the cDNAs encoding for bovine as described by Dahlback et al., *Proc. Natl. Acad. Sci., U.S.A.*, 78:2512–2516 (1986) and human protein S as described by Lundwall et al., *Proc. Natl. Acad. Sci., U.S.A.*, 83:6716–6720 (1986); Hoskins et al., *Proc. Natl. Acad. Sci., U.S.A.*, 84:349–335 (1984) and Ploos van Amstel, *FEBS Lett.*, 222:186–190 (1987), it is inferred that PS is synthesized as a single chain molecule. Protein S consists of a leader sequence followed by protein modules homologous to a carboxyglutamic acid domain, a thrombin sensitive domain, four epidermal growth factor-like domains and a sex hormone binding globulin-like domain.

In human PS, the thrombin-sensitive domain contains three potential cleavage sites for thrombin, namely after Arg-49, Arg-60 and Arg-70. Which of these is actually cleaved and what the effect of cleavage for the APC cofactor activity is, is not known. Bovine and human protein S have been reported to be very sensitive to proteolysis by thrombin. See, Mitchell et al., *Thromb. Haemost.*, 56:151–154 (1986); Dahlback et al., *J. Biol. Chem.*, 261:5111–5115 (1986); Dahlback, *Biochem. J.*, 209:837–846 (1983) and Morita et al., *J. Biol. Chem.*, 99:561–568 (1986). In bovine PS thrombin cleaves after Arg-52 and Arg-70, thus producing a two-chain molecule linked together by a disulfide bond between Cys-47 to Cys-72. Thrombin-cleaved PS has lost its APC cofactor activity. Therefore, it has been proposed that this cleavage may represent a physiological mechanism for the control of the PS cofactor activity to APC; however physiological concentrations of calcium might protect PS against cleavage.

Because most of the purified PS preparations contain a variable amount of two-chain PS, it is very difficult to use these preparation for the quantitative evaluation of functional aspects of purified PS. Therefore, a PS variant was designed that is resistant to thrombin cleavage but still retains full APC cofactor activity and binding affinity for C4BP. The following seven recombinant variants were constructed as described in Example 1B2), where the arginines were replaced by leucine or isoleucine: three single variants (R49L, R60L and R70I), three double variants (R49L/R60L, R60L/R70I and R49L/R70I) and one triple variant (R49L/R60L/R70I). The terminology for designating each of the variants is described in Example 1B1).

A. Assaying of Cofactor Activity with APC

The ability of the variants to serve as a cofactor for APC was tested in a clotting assay. The clotting assay was performed as described in Example 2D. To examine the effects of thrombin on recombinant PS variants APC cofactor activity, one ml of purified recombinant PS variants listed above and prepared in Example 1D (4-40 ug/ml) was maintained with 1/20 vol (50 ul) of thrombin-Sepharose for 1 hour at 37C. in 50 mM Tris-HCl pH 7.5 containing 150 mM CaCl. Thrombin-Sepharose was removed by centrifugation. Supernatants containing the thrombin-treated PS were stored at −20C. until used.

As shown in Table 3, recombinant wild-type PS and all PS variants showed APC cofactor activity. When the proteins were treated with thrombin, this APC cofactor activity was lost except in the case of the triple variant, which retained its APC cofactor activity. This demonstrates that cleavage at each of the three arginine residues resulted in a loss of APC cofactor activity. From these experiments it cannot be concluded whether all three cleavage sites are equally sensitive for the action of thrombin.

TABLE 3

| Time Variant | Concentration (ug/ml) | Clotting Time (sec) | Clotting After Treatment |
|---|---|---|---|
| R49L | 0.60 | 80 | 72 |
| R60L | 2.38 | 90 | 75 |
| R70I | 0.60 | 79 | 75 |
| R49L/R60L | 1.12 | 88 | 80 |
| R60L/R70I | 0.60 | 79 | 72 |
| R49L/R70I | 1.12 | 86 | 80 |
| R49L/R60L/R70I | 1.19 | 84 | 85 |
| Recombinant | 2.38 | 91 | 70 |

APC cofactor activity of the variants (final concentration: 0.60-2.38 ug/ml) was determined in a clotting assay as described above. The clotting time in the absence of protein S is 72 ± 2 seconds. Numbering of the amino acid residues is according to refs. 12-19. R = arginine (arg), L = leucine (leu), I - isoleucine (ile).

The PS-dependent prolongation of the clotting time was measured in an activated partial thromboplastin time system using PS and C4BP depleted plasma, APC and cephalin-kaolin reagent as described in Example 2D. Increasing amounts of recombinant PS or the triple variant treated without or with thrombin were added. Clotting was initiated by the addition of $CaCl_2$ and the clotting time was measured. The results are presented as the means of duplicate values.

Figure 2:
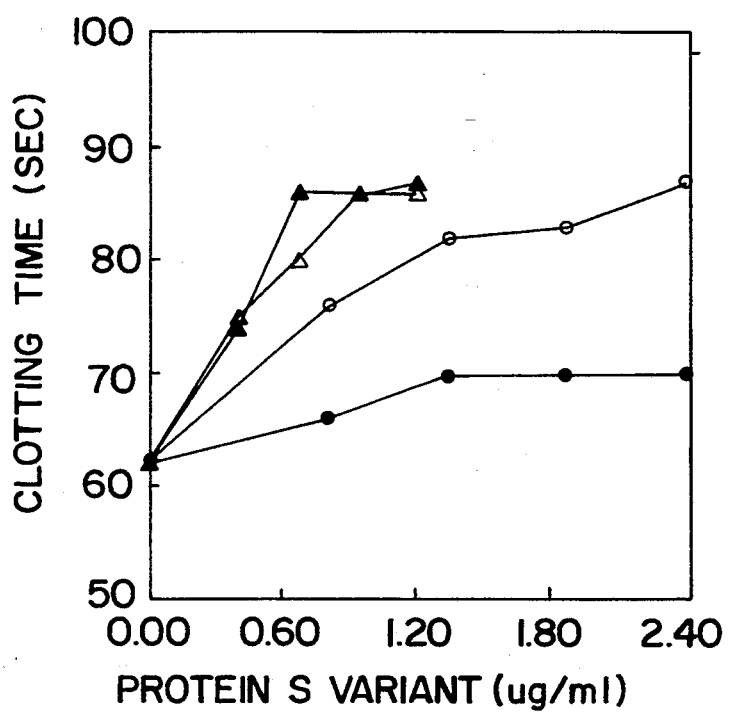

The results of this dose-response curve of the APC cofactor activity of recombinant PS and the triple variant is shown in FIG. 2. At each concentration tested, the triple variant showed a higher APC cofactor activity (as defined by prolongation of the clotting time) than recombinant PS. This is most likely due to the absence of cleaved PS in the triple variant preparation in contrast to cleaved PS present in the preparation of recombinant wild type PS. Upon treatment with thrombin, the dose-response curve of the triple variant remained unchanged, whereas the APC cofactor activity of recombinant PS was significantly decreased.

The single and double variants also had APC cofactor activity (Table 3). As determined by gel electrophoresis as performed in Example 2E, varying amounts of the single and two-chain forms of PS were present in the preparations. Treatment of these preparation with thrombin followed by analysis on reduced SDS gels indicated that the upper migrating band present in each preparation was converted into the lower band.

The thrombin cleavage sites in bovine PS were identified using amino acid terminal sequences of the isolated bovine PS fragments obtained after thrombin treatment as described by Dahlback et al., *J. Biol. Chem.*, 261:5111–5115 (1986) Three bovine PS fragments were identified: Ala-1 to Arg-52, Ala-53 to Arg-70 and Ser-71 to Ser-635, indicating that the cleavage sites were located after Arg-52 and Arg-70. Human PS, thus, can be cleaved by thrombin after Arg-49, Arg-60 and Arg-70. Human and bovine PS share 82% homology between Cys-47 and Cys-72 in the thrombin-sensitive domain and both proteins contain three arginine residues in this region. Therefore, it remains possible that bovine PS can also be observed on SDS gels, between Ala-1 to Arg-52 and Ala-1 to Arg-70, that could represent the Ala-1 to Arg-60 fragment.

B. Binding of Recombinant Wild-type PS and PS Variants to C4BP

The binding of the of the thrombin domain recombinant PS variants to C4BP was determined. The complex formation between the recombinant proteins and C4BP was measured with a sensitive ELISA using anti-C4BP monoclonal antibody 8C11 IgG, purified C4BP and peroxidase conjugated anti-PS antibody as described in Example 2A.

Anti-C4BP monoclonal antibody 8C11 IgG was coated onto microtiter wells to catch C4BP (1 ug/ml). Increasing amounts (0–100 ng/ml) of recombinant PS or variants (R49L, R60L, R70I, R49L/R60L, R60L/R70I, R49L/R70I and R49L/R60L/R70I) were added. Binding to C4BP was for 18 hours at room temperature. Bound PS variants were detected with anti-PS IgG conjugated to peroxidase (0.3 ug/ml). The results are the mean of duplicate values in two different experiments.

Figure 3:
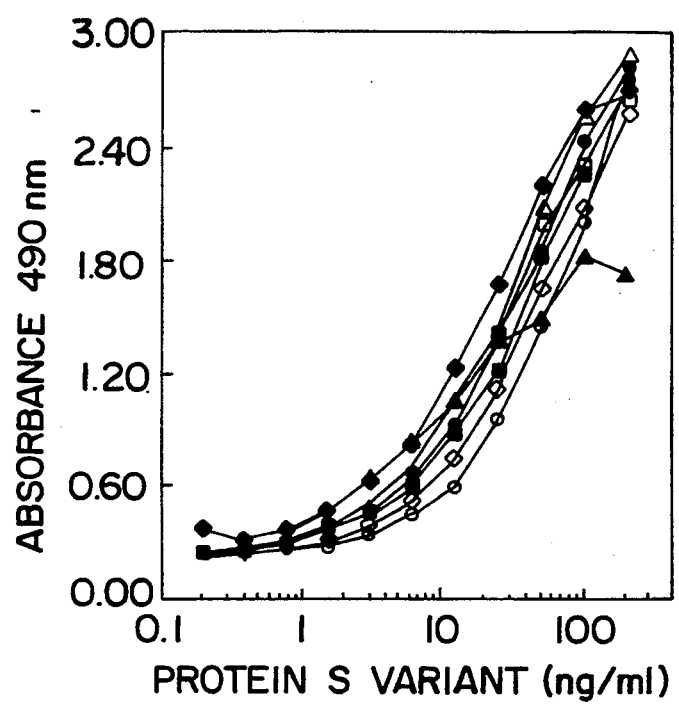

The results, presented in FIG. 3, show that in the presence of calcium all seven variants bound to C4BP with the same affinity as wild type PS. This suggests that the alteration of the arginine residues does not influence the binding affinity of PS for binding to C4BP, and that the binding site(s) on the PS molecule for C4BP are still available. In conclusion, a PS variant (the triple variant) was discovered that was completely resistant to inactivation by thrombin, that still retained full APC cofactor activity and that had an unaltered affinity for binding to C4BP. This variant will be very useful for the quantitative studies of the APC cofactor activity of PS without interference of thrombin. In addition, the triple variant can be used for standardization of the APC cofactor activity of PS.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A variant protein S (vPS) having at least 95% amino acid residue sequence identity with wild-type mature human protein S having the amino acid residue sequence shown in SEQ ID NO 2, said wild-type mature human protein S having a capacity to bind C4b binding protein (C4BP), and said vPS having in vitro anticoagulant activity and a capacity to bind C4BP that is less than 90% of the C4BP binding capacity of wild-type mature human protein S, wherein said vPS has an amino acid residue substitution selected from the group consisting of K429E, I425A/I426A and K432E.

2. The variant protein S of claim 1 wherein said protein has an amino acid residue sequence consisting of the sequence shown in SEQ ID NO 2 with the substitution K429E.

3. The variant protein S of claim 1 wherein said protein has an amino acid residue sequence consisting of the sequence shown in SEQ ID NO 2 with the substitution I425A/I426A.

4. The variant protein S of claim 1 wherein said protein has an amino acid residue sequence consisting of the sequence shown in SEQ ID NO 2 with the substitution K432E.

* * * * *